US009492209B2

(12) United States Patent
Biedermann et al.

(10) Patent No.: US 9,492,209 B2
(45) Date of Patent: Nov. 15, 2016

(54) EXTENSION DEVICE FOR A BONE ANCHOR, IN PARTICULAR FOR MINIMALLY INVASIVE SURGERY

(71) Applicant: Biedermann Technologies GmbH & Co. KG, Donaueschingen (DE)

(72) Inventors: Timo Biedermann, Trossingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/565,365

(22) Filed: Dec. 9, 2014

(65) Prior Publication Data
US 2015/0182265 A1  Jul. 2, 2015

Related U.S. Application Data

(60) Provisional application No. 61/913,777, filed on Dec. 9, 2013, provisional application No. 62/013,415, filed on Jun. 17, 2014.

(30) Foreign Application Priority Data

Dec. 9, 2013  (EP) .................................... 13196326

(51) Int. Cl.
*A61B 17/70*  (2006.01)
*A61B 17/00*  (2006.01)
(52) U.S. Cl.
CPC ..... *A61B 17/7085* (2013.01); *A61B 17/00234* (2013.01); *A61B 17/7032* (2013.01); *A61B 17/708* (2013.01); *A61B 17/7091* (2013.01)
(58) Field of Classification Search
CPC .......... A61B 17/7082; A61B 17/7037; A61B 17/7076; A61B 17/708; A61B 17/7085; A61B 17/7091

USPC ......................... 606/86 A, 279, 104, 99, 914
See application file for complete search history.

(56) References Cited

U.S. PATENT DOCUMENTS 7,563,264 B2  7/2009  Landry et al.
8,211,110 B1  7/2012  Corin et al.
(Continued)

FOREIGN PATENT DOCUMENTS

WO  WO 2013/112689 A2  8/2013
WO  WO 2013/187928 A1  12/2013

OTHER PUBLICATIONS

European Search Report and Opinion issued by the EPO for EP 13196326.6 on Jun. 5, 2014 (7 pages).
(Continued)

*Primary Examiner* — Pedro Philogene
*Assistant Examiner* — David C Comstock
(74) *Attorney, Agent, or Firm* — Lewis Roca Rothgerber Christie LLP

(57) ABSTRACT

An extension device for a bone anchor is provided, where the bone anchor includes an anchoring section for anchoring to a bone and a receiving part connected to the anchoring section. The receiving part includes a central axis and a channel for receiving a rod, where sidewalls of the channel form two free legs. The extension device includes a first sleeve with a first sleeve axis that is coaxial with the central axis, where the first sleeve is configured to be detachably coupled to the receiving part. The extension device includes a second sleeve with a second sleeve axis, where the second sleeve is positioned within the first sleeve. The first sleeve is configured to be coupled to the receiving part to inhibit translational movement of the first sleeve relative to the receiving part along the central axis. The second sleeve is configured to be coupled to the receiving part to hinder or inhibit rotational movement of the second sleeve relative to the receiving part and the second sleeve is connected to the first sleeve through a coupling member that is configured to advance in the first sleeve together with the second sleeve in an axial direction.

22 Claims, 13 Drawing Sheets

(56) References Cited

U.S. PATENT DOCUMENTS

| | | |
|---|---|---|
| 8,439,922 B1 | 5/2013 | Arnold et al. |
| 2005/0131408 A1* | 6/2005 | Sicvol ................ A61B 17/7091 606/86 A |
| 2008/0125788 A1 | 5/2008 | Cohen et al. |
| 2012/0022594 A1 | 1/2012 | Walker et al. |
| 2014/0039567 A1 | 2/2014 | Hoefer et al. |
| 2014/0052187 A1 | 2/2014 | McBride et al. |

OTHER PUBLICATIONS

European Search Report; Application Serial No. 14172835.2; dated Jan. 29, 2015; 13 sheets.

* cited by examiner

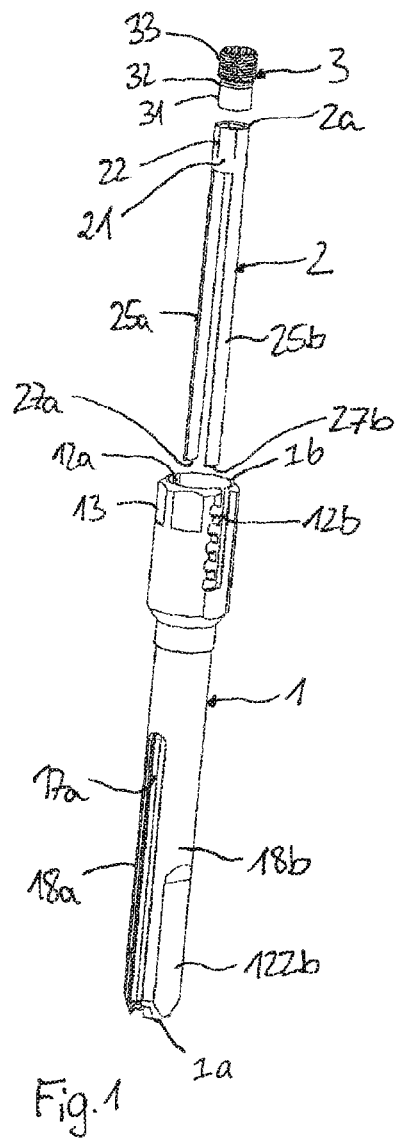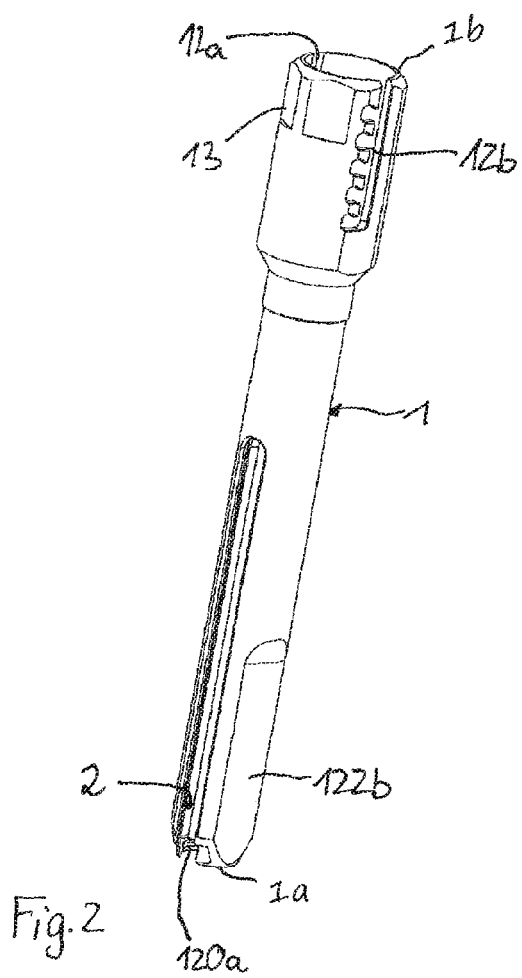
Fig. 1
Fig. 2

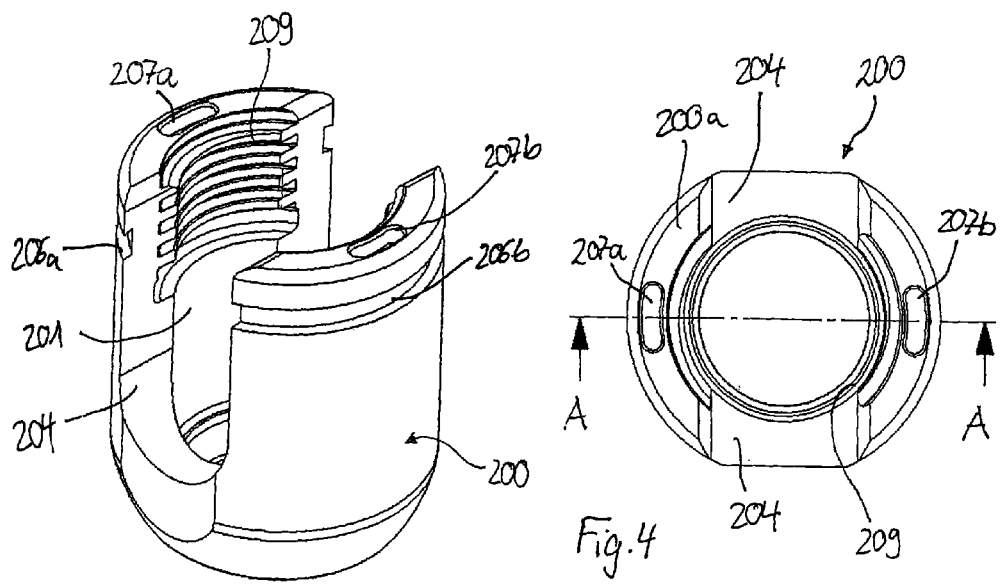
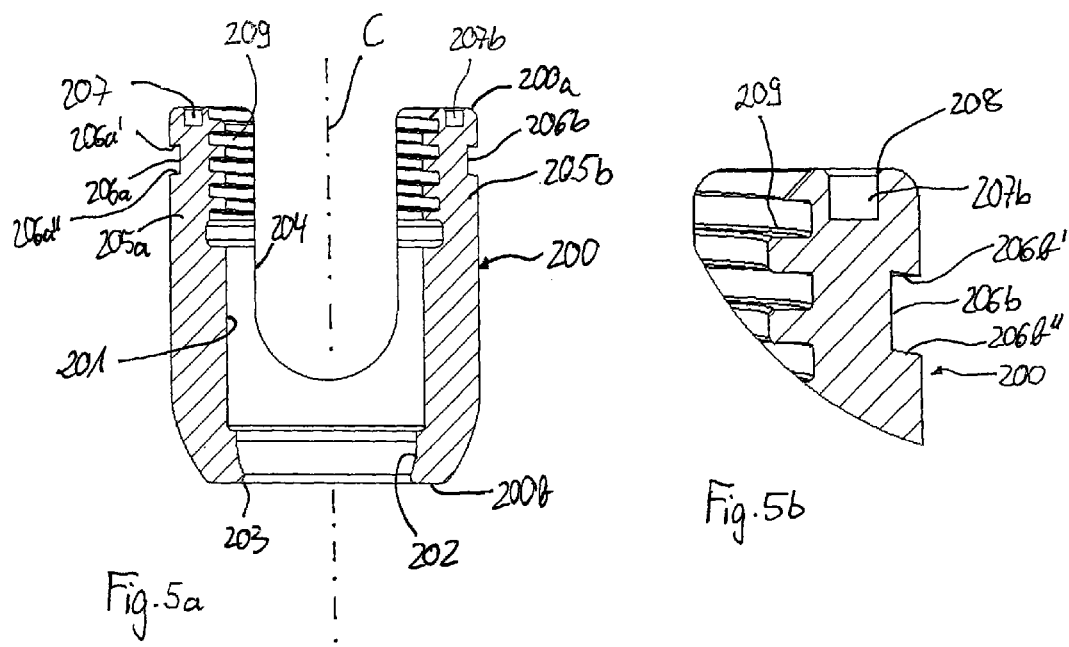

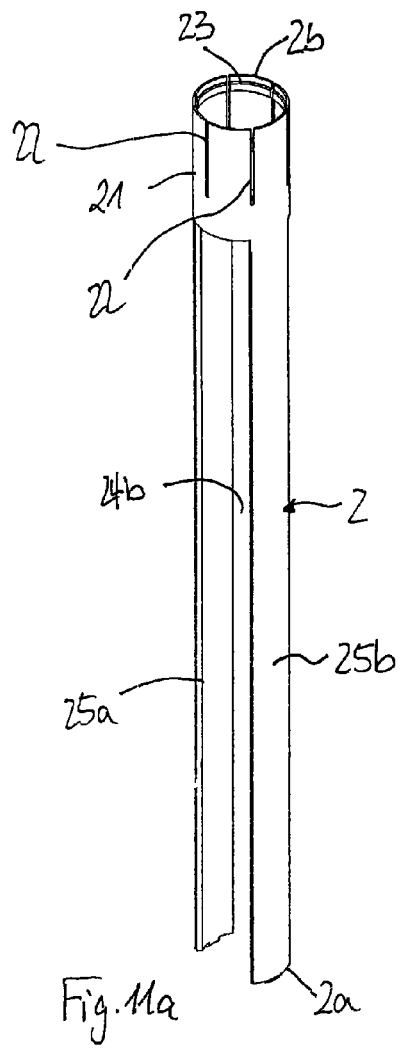
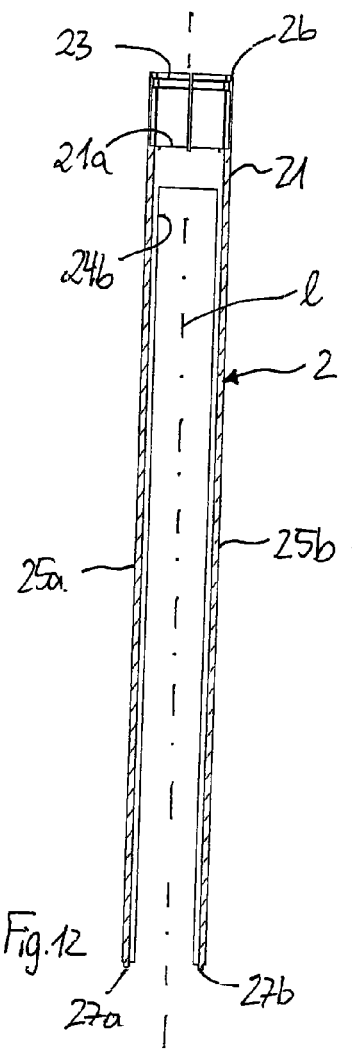
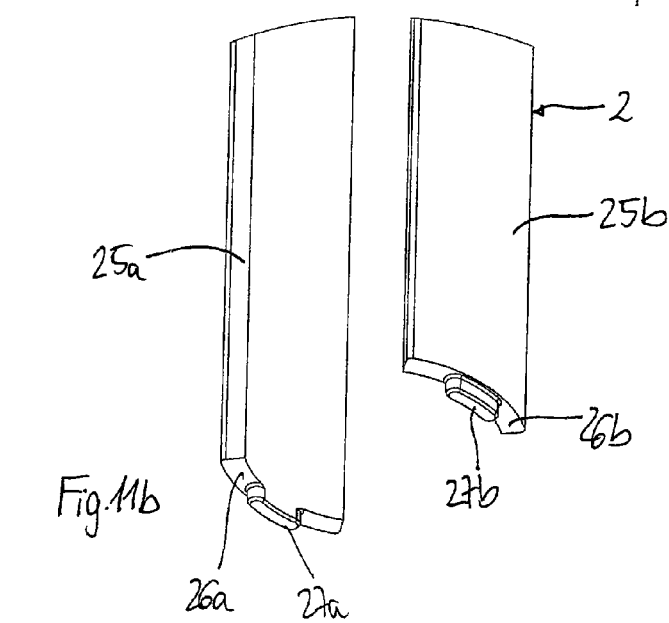

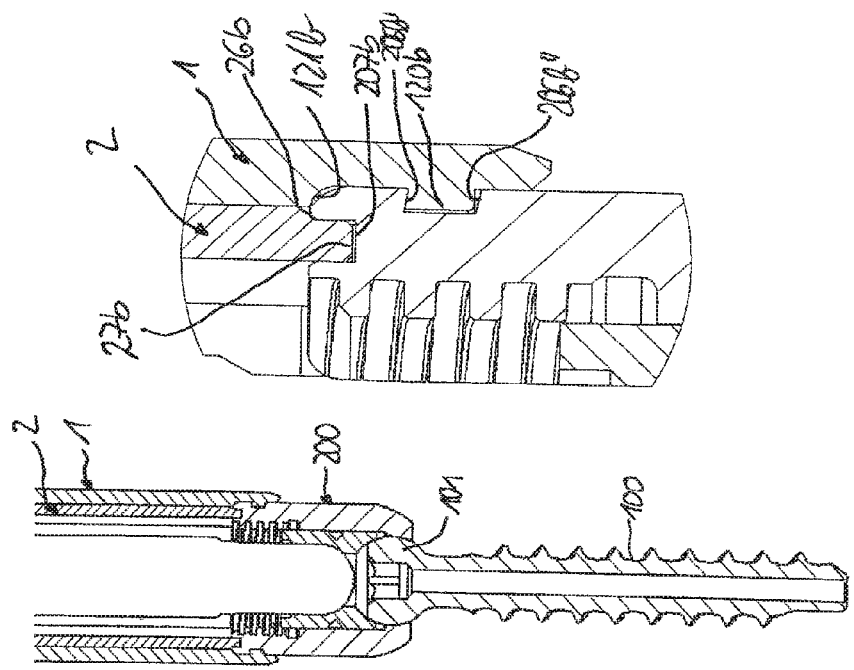
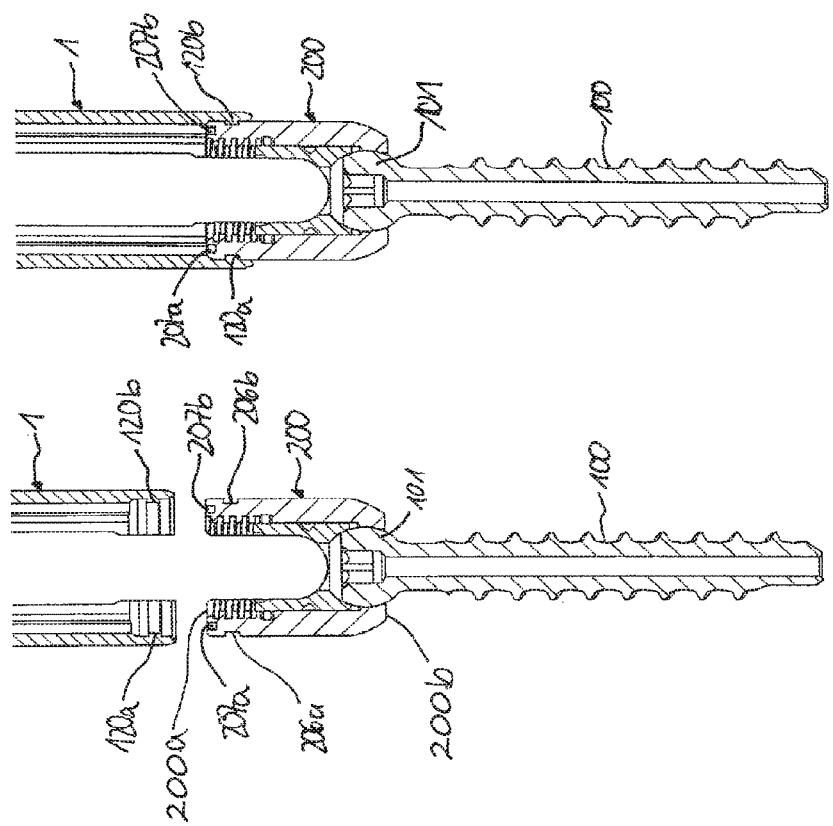

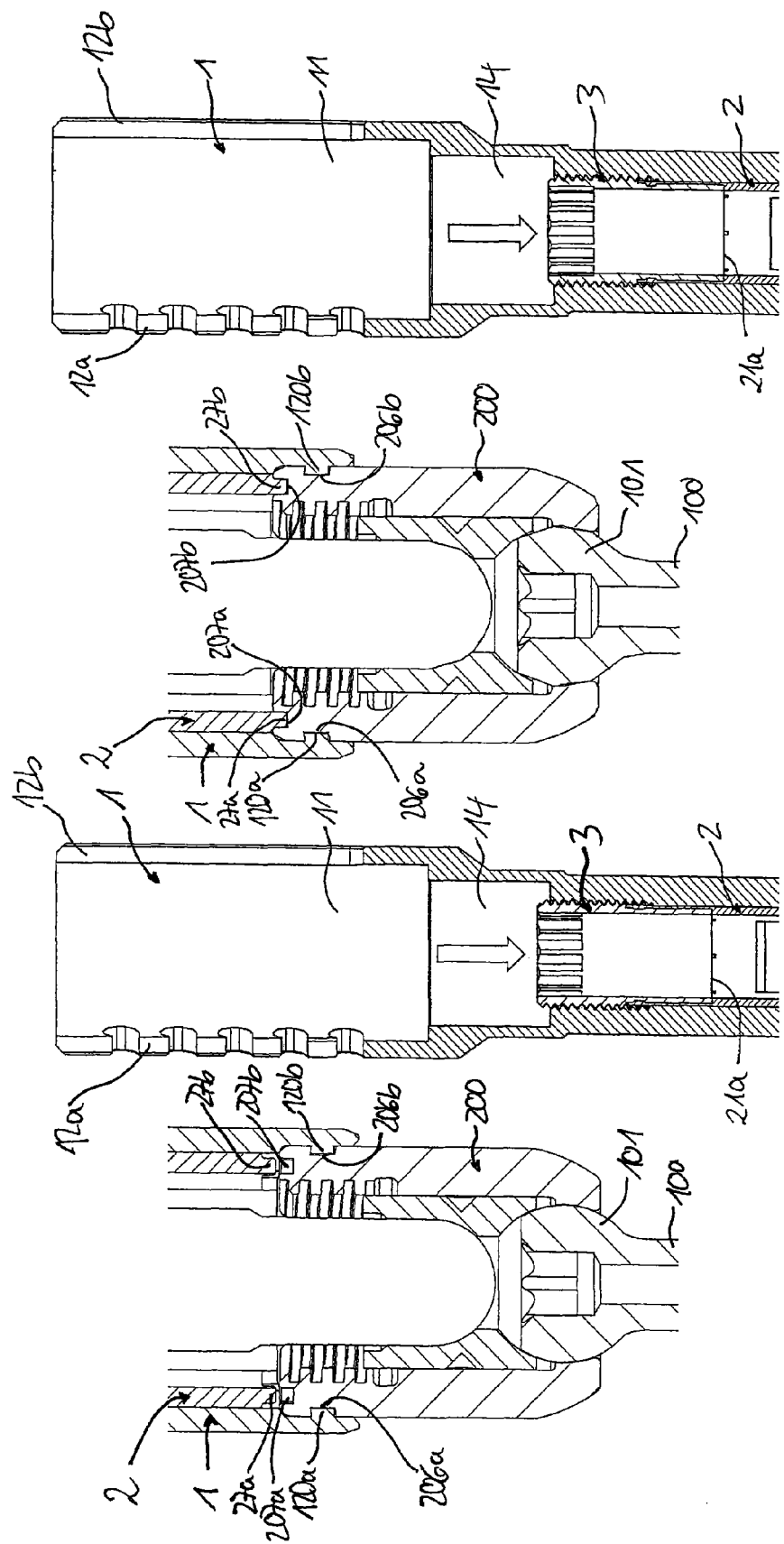

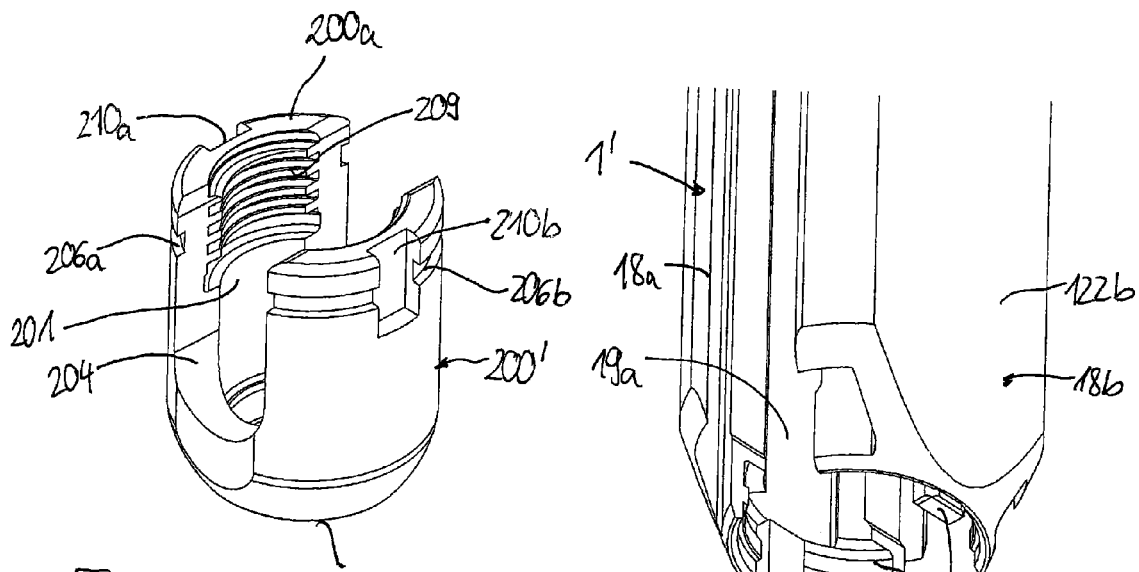
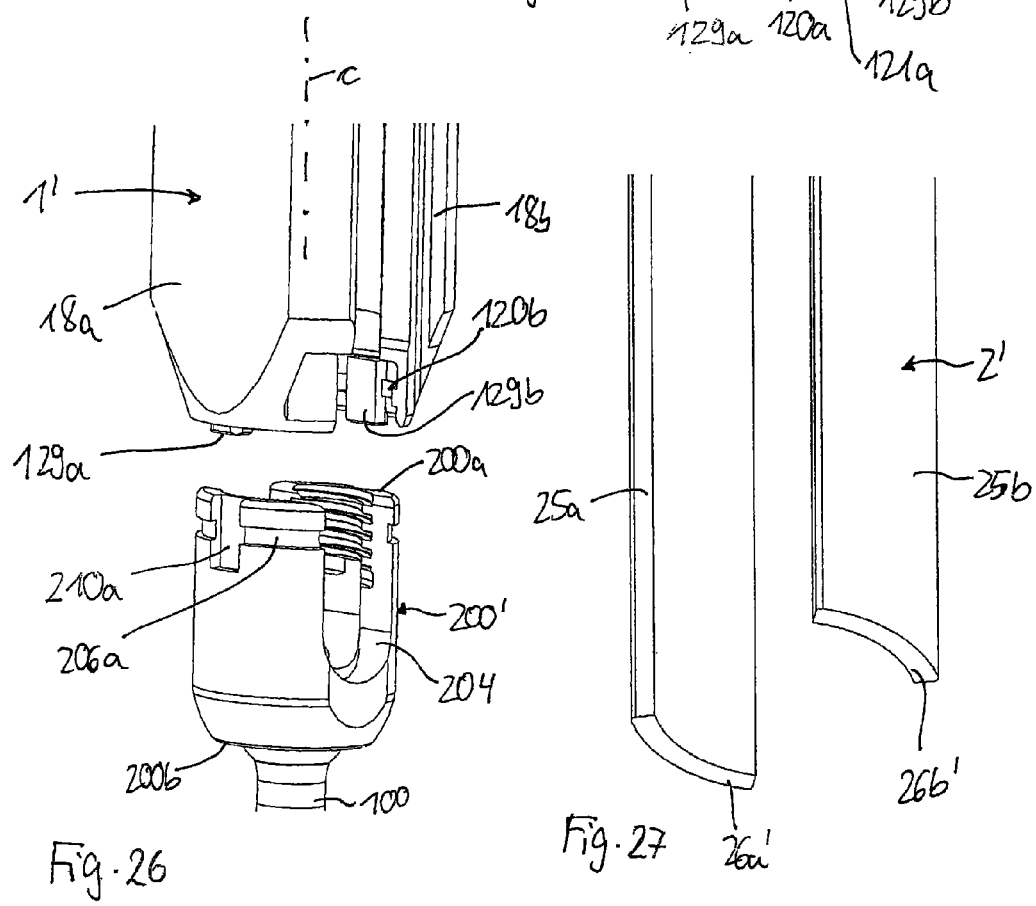

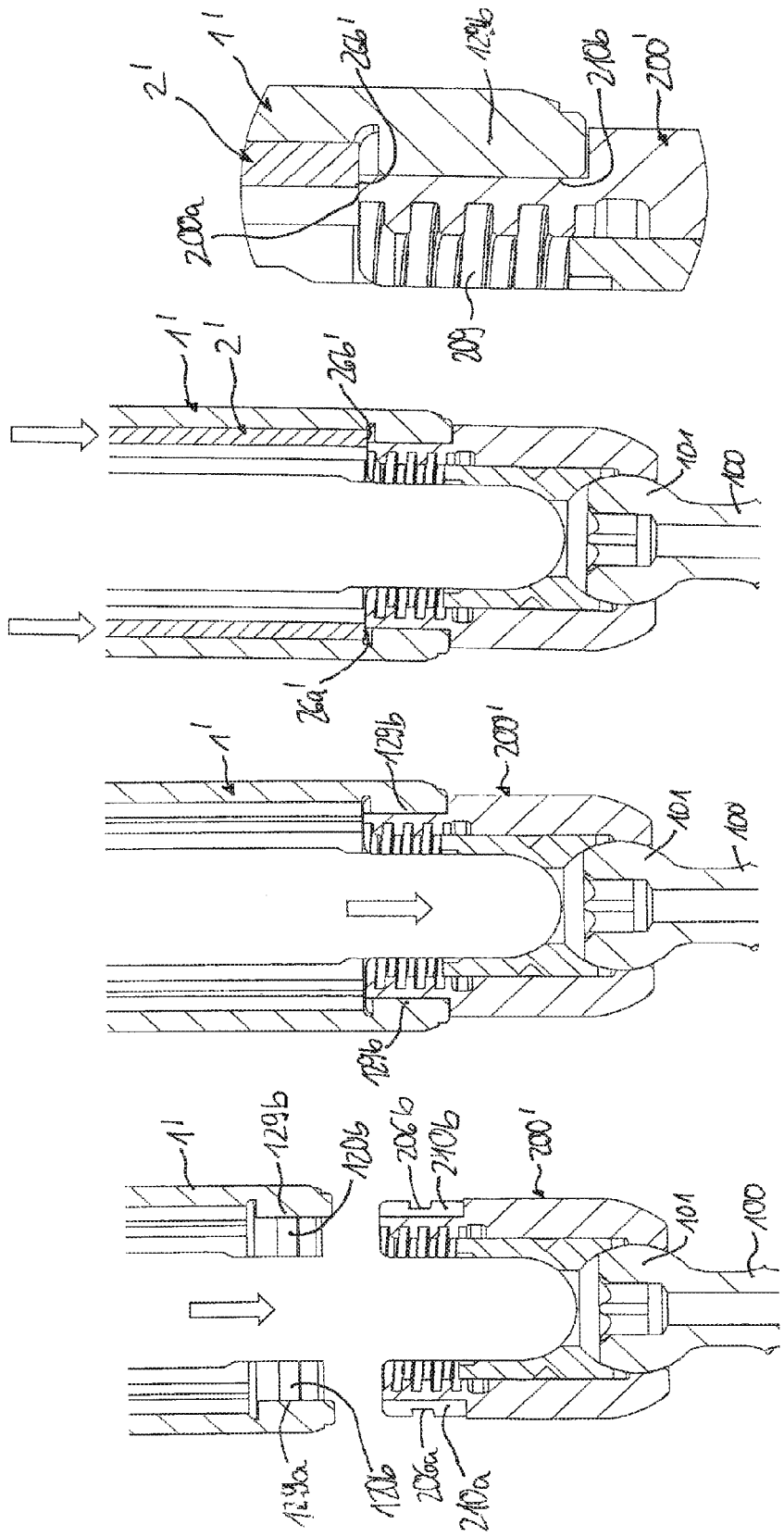

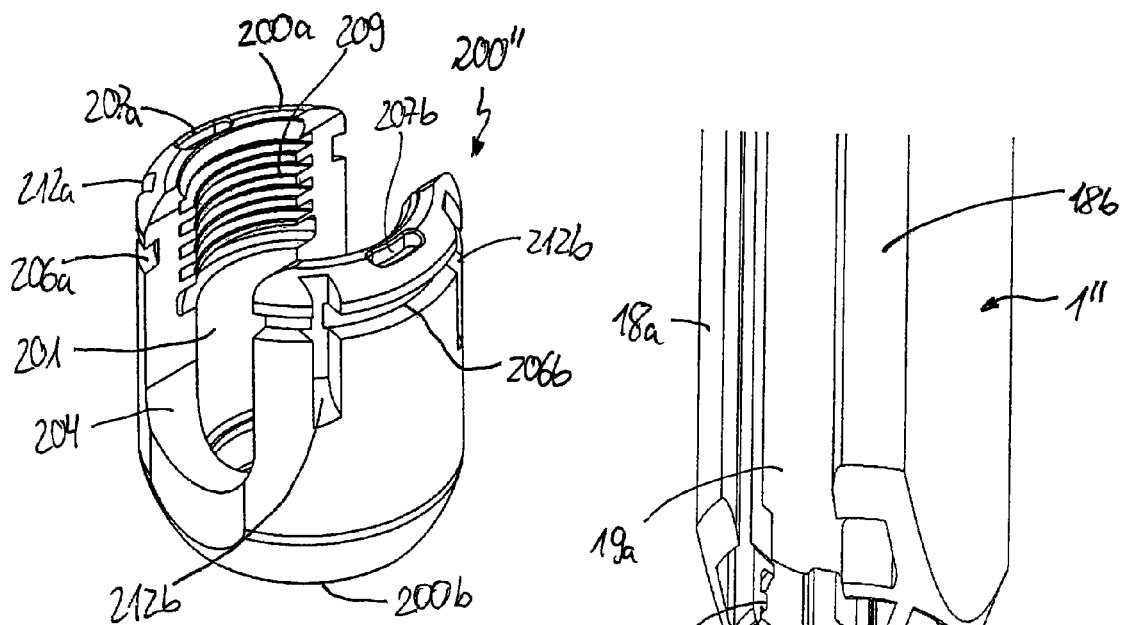
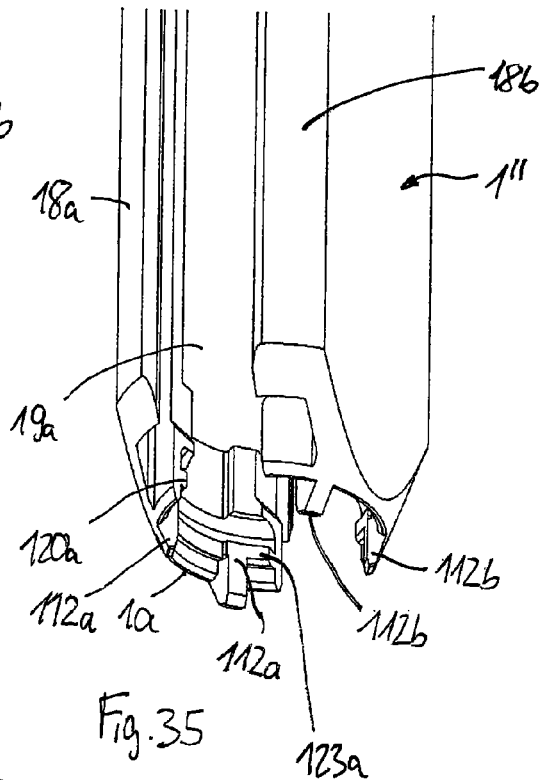
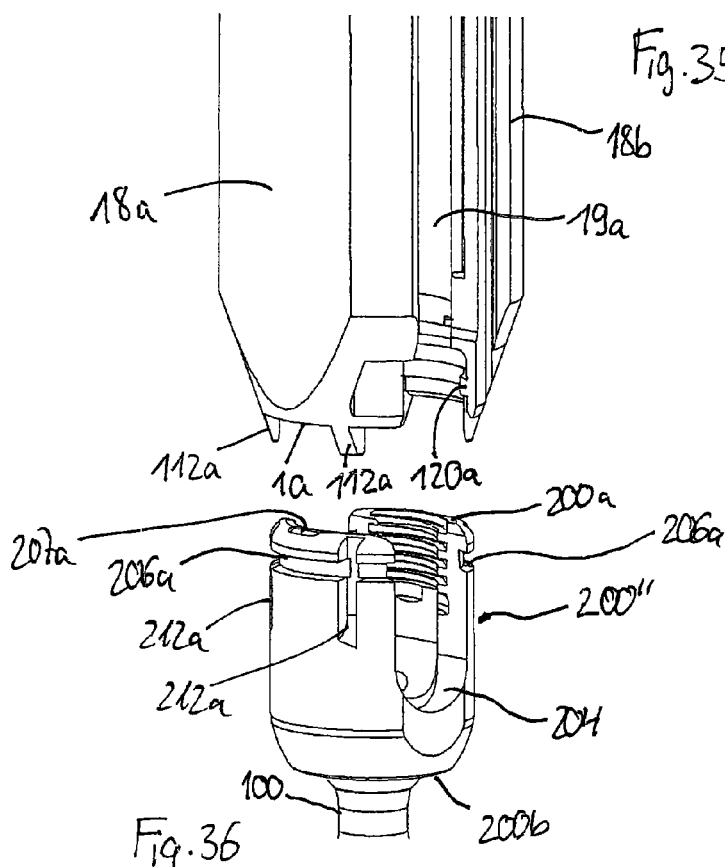
Fig. 34
Fig. 35
Fig. 36

US 9,492,209 B2

EXTENSION DEVICE FOR A BONE ANCHOR, IN PARTICULAR FOR MINIMALLY INVASIVE SURGERY

CROSS-REFERENCE TO RELATED APPLICATIONS

The present disclosure claims the benefit of U.S. Provisional Patent Application Ser. No. 61/913,777, filed Dec. 9, 2013, the contents of which are hereby incorporated by reference in their entirety, claims the benefit of U.S. Provisional Patent Application Ser. No. 62/013,415, filed Jun. 17, 2014, the contents of which are hereby incorporated by reference in their entirety, and claims priority from European Patent Application EP 13196326.6, filed Dec. 9, 2013, the contents of which are hereby incorporated by reference in their entirety.

BACKGROUND

Field

The present disclosure relates to an extension device for a bone anchor, in particular for use in minimally invasive surgery (MIS). The present disclosure also relates to a system including such an extension device and a bone anchor, where the bone anchor includes an anchoring section and a receiving part for receiving a rod to couple the rod to the anchoring section. The extension device includes a first sleeve and a second sleeve positioned within the first sleeve. The extension device also includes a coupling structure that allows the extension device to couple to the receiving part of the bone anchor and that inhibits translational and rotational movement of the extension device relative to the receiving part.

Description of Related Art

Extension devices, also called head extenders, for pedicle screws for use in minimally invasive surgery are known in the art. For example, U.S. Pat. No. 7,563,264 B2 describes a spinal stabilization system for a minimally invasive procedure wherein detachable sleeves may be coupled to a collar of a bone anchor to allow for formation of the spinal stabilization system through a small skin incision. The detachable sleeve members may allow for alignment of the collars to facilitate insertion of an elongated member in the collars. A coupling system is provided between the sleeve and the collar that inhibits translational movement of the sleeve relative to the collar. In one embodiment, the sleeve may be coupled to a collar of a bone fastener assembly with movable members that may be threaded into threaded openings in the collar.

WO 2013/112689 A2 describes a minimally invasive tower access device comprising an elongated outer sleeve that slidably receives an elongated inner sleeve. A lock nut is used to secure the inner sleeve and outer sleeve in a locked mode.

SUMMARY

Embodiments of the invention provide an improved extension device or head extender for a bone anchor, in particular for use in minimally invasive surgery. Embodiments of the invention also provide a system including such an extension device and a bone anchor that facilitates surgical procedures and improves the safety of surgical measures such as compression and distraction.

In one or more embodiments, the extension device may be coupled to a receiving part such that the extension device is locked against translational and rotational movement relative to the receiving part. Because translational and rotational movements of the extension device relative to the receiving part are inhibited, the connection between the extension device and the receiving part is more robust. The more securely coupled extension device and receiving part permit a safe placement of a rod and a set screw for fixing the rod, as well as facilitate surgical steps of adjustment of the spinal stabilization system, such as compression or distraction. These surgical steps may be performed using the extension device attached to the receiving part.

In one or more embodiments, the extension device includes a first sleeve, a second sleeve positioned within the first sleeve, and an interlocking bushing that connects the second sleeve to the first sleeve and provides a controlled axial movement of the second sleeve relative to the first sleeve. After the extension device has been attached to the receiving part, the first sleeve and the second sleeve can be interlocked to each other and to the receiving part by moving the interlocking bushing in a first direction. The interlocking connection between the first sleeve and the second sleeve can be released by moving the interlocking bushing in a direction opposite to the first direction.

In one or more embodiments, translational movement between the extension device and the receiving part can be inhibited by a form-fit engagement of a circumferential rib that extends at least partially around a longitudinal axis of the extension device and engages a corresponding circumferential groove. The first sleeve may include the rib and the receiving part may include the groove, or vice versa.

In one or more embodiments, a rotational movement between the extension device and the receiving part may be inhibited by the engagement of a longitudinal rib that engages a longitudinal groove. The first and/or the second sleeve may include the rib and the receiving part may include the groove, or vice versa. The form-fit connection of the longitudinal ribs and grooves allows the application of a high torque to the receiving part.

The extension device may include only a few parts to facilitate the assembly and operation of the device.

BRIEF DESCRIPTION OF THE DRAWINGS

Further features and advantages of the invention will become apparent from the description of embodiments using the accompanying drawings. In the drawings:

FIG. 1 shows a perspective exploded view of an extension device according to a first embodiment;

FIG. 2 shows a perspective view of the extension device of FIG. 1 in an assembled state;

FIG. 3 shows a perspective view of a first embodiment of a receiving part of a polyaxial bone anchor that, together with the extension device of FIGS. 1 and 2, may form a first embodiment of a system including the extension device and the bone anchor;

FIG. 4 shows a top view of the receiving part of FIG. 3;

FIG. 5a shows a cross-sectional view of the receiving part of FIG. 3, the cross-section taken along line A-A in FIG. 4;

FIG. 5b shows an enlarged view of a detail of FIG. 5a;

FIG. 11a shows a perspective view of a second sleeve of the extension device of FIGS. 1 and 2;

FIG. 11b shows an enlarged perspective view of a detail of FIG. 11a;

FIG. 12 shows a cross-sectional view of the second sleeve of FIG. 11a, the cross-section taken in a plane containing a longitudinal axis of the second sleeve and extending through a center of legs of the second sleeve;

FIG. 15 shows a perspective view of a first step of assembling the extension device of FIGS. 1 and 2, where the interlocking bushing of FIG. 13 is to be mounted to a rear end section of the second sleeve of FIG. 11a;

FIGS. 17 to 19a show cross-sectional views of steps of attaching the extension device of the first embodiment to a polyaxial bone anchor;

FIG. 19b shows an enlarged view of a detail of FIG. 19a;

FIG. 20 shows a cross-sectional view of the bone anchor and attached extension device according to the first embodiment in a state before the extension device is rotationally locked with respect to the bone anchor;

FIG. 21 shows a cross-sectional view of an upper portion of the extension device in the state shown in FIG. 20;

FIG. 22 shows a cross-sectional view of the bone anchor and attached extension device according to the first embodiment in a state where the extension device is rotationally locked with respect to the bone anchor;

FIG. 23 shows a cross-sectional view of an upper portion of the extension device in the state shown in FIG. 22;

FIG. 24 shows a perspective view of a receiving part of a polyaxial bone anchor according to a second embodiment that, together with an extension device according to a second embodiment, forms a second embodiment of a system including the extension device and the bone anchor;

FIG. 25 shows an enlarged perspective view of a front end portion of a first sleeve of the extension device according to the second embodiment;

FIG. 26 shows a perspective view of the front end portion of the first sleeve of the extension device according to the second embodiment and a polyaxial bone anchor with the receiving part according to the second embodiment shown in FIG. 24;

FIG. 27 shows an enlarged perspective view of a front end portion of a second sleeve of the extension device according to the second embodiment;

FIGS. 28 to 30a show cross-sectional views of steps of attaching the extension device according to FIGS. 25 to 27 to the polyaxial bone anchor according to the second embodiment;

FIG. 30b shows an enlarged view of a detail of FIG. 30a;

FIG. 34 shows a perspective view of a receiving part of a bone anchor according to a third embodiment that, together with an extension device according to a third embodiment, forms a third embodiment of a system including the extension device and the bone anchor;

FIG. 35 shows an enlarged perspective view of a front end portion of a first sleeve of the extension device according to the third embodiment;

FIG. 36 shows a perspective view of the front end portion of the extension device according to the third embodiment and a polyaxial bone anchor with the receiving part according to the third embodiment shown in FIG. 34;

DETAILED DESCRIPTION

Figure 6:
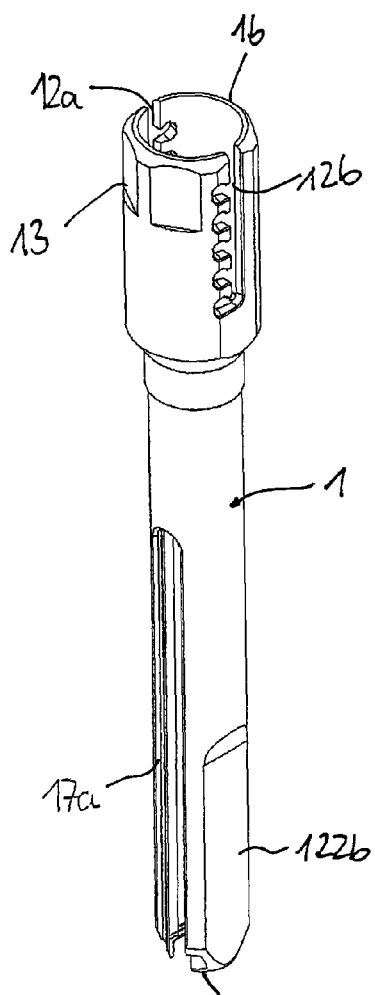
FIG. 6 shows a perspective view of a first sleeve of the extension device of FIGS. 1 and 2.
Figure 8:
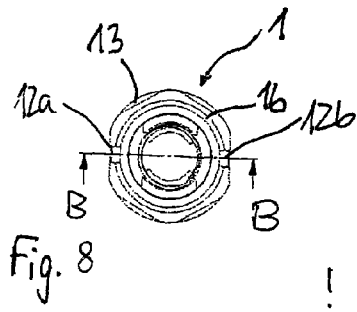
FIG. 8 shows a top view of the first sleeve of FIG. 6.

Referring to FIGS. 1 and 2, an extension device or head extender according to a first embodiment includes a first sleeve 1 that forms an outer sleeve, a second sleeve 2 that forms an inner sleeve and that is positionable within the first sleeve 1, and an interlocking bushing 3. The interlocking bushing 3 is configured to be connected to the second sleeve 2 and is configured to couple the second sleeve 2 to the first sleeve 1 and to permit a controlled motion of the second sleeve 2 relative to the first sleeve 1.

The extension device shown in FIGS. 1 and 2 is configured to be used with a polyaxial bone anchor, an embodiment of which will be explained first. An example of such a bone anchor includes an anchoring element with a threaded shank 100 and a spherical segment shaped head 101, for example, as shown in FIGS. 17 to 19a, where the anchoring element is pivotably coupled to a receiving part 200. The receiving part 200 is shown more in detail in FIGS. 3 to 5b. The receiving part 200 may be a substantially cylindrical part with a first end or top end 200a, a second or bottom end 200b, a central axis C, a coaxial bore 201 extending from the top end 200a to a distance from the bottom end 200b, a seat 202 for the head 101 of the anchoring element, and a lower opening 203 at the bottom end 200b through which the threaded shank 100 of the bone anchoring element can pass through. A substantially U-shaped recess 204 extends from the top end 200a toward the bottom end 200b. The recess 204 serves for receiving a rod (not shown). By means of the recess 204, two free legs 205a, 205b are formed. Circumferentially extending grooves 206a, 206b are formed at an outer surface of the legs 205a, 205b at a distance from the top end 200a. The circumferentially extending grooves 206a, 206b extend from one end of a channel formed by the U-shaped recess 204 to a second end of the channel and are open toward the U-shaped recess 204. Upper side walls 206a', 206b' and lower side walls 206a'', 206b'' of the grooves 206a, 206b may have a shape that is inclined and increases in diameter or width toward the top end 200a of the receiving part 200, as shown, for example, in FIG. 5b.

The receiving part 200 further includes one or more recesses 207a, 207b at the top end 200a at a free end surface of each of the legs 205a, 205b, the recesses 207a, 207b extending into the legs 205a, 205b in a direction coaxial to the central axis (C). In a top view of the receiving part 200 (see, e.g., FIG. 4), the recesses 207a, 207b are elongated and closed at both ends in a circumferential direction. As can be seen in particular in FIG. 5b, a cross-section of the recesses 207a, 207b may be substantially square or rectangular. The recesses 207a, 207b serve to engage a portion of the extension device, as further described below. Toward the top end 200a, a chamfered section 208 may be provided at each recess 207a, 207b to facilitate engagement of the recesses 207a, 207b with a corresponding protrusion of the extension device.

In an upper portion of the legs 205a, 205b, an internal thread 209 is provided for cooperation with a locking screw (not shown) for fixing the rod.

Referring to FIGS. 6 to 10, the first sleeve 1 of the extension device includes a longitudinal axis c that is coaxial with the central axis C of the receiving part 200 when the extension device is coupled to the receiving part. The first sleeve 1 further has a front end or distal end 1a and a rear end or proximal end 1b.

Adjacent to the rear end 1b, the first sleeve 1 includes a first section 11 with a larger inner diameter compared to other sections of the first sleeve 1. Two slits 12a, 12b extend from the rear end 1b along at least a portion of the first section 11 in a longitudinal direction parallel to the longitudinal axis c. One of the sidewalls of each longitudinal slit 12a, 12b includes a wavy structure, as can be seen in particular in FIG. 6, for latching with a reduction sleeve (not shown) used for further steps in the surgical procedure, for example for pressing down the rod and inserting a locking screw to fix the rod. Furthermore, an engagement structure or portion 13, which may include, for example, a plurality of flat engagement portions, is provided at an outer surface of the first section 11 for engagement with a tool. Following the first section 11, the first sleeve 1 includes a second section 14 with slightly smaller inner diameter than the first section 11. Adjacent to the second section 14 is a third section 15 with a smaller inner diameter compared to the second section 14 and first section 11. A threaded section 16 is provided in the third section 15 that is configured to cooperate with the interlocking bushing 3, as further described below.

Figure 9:
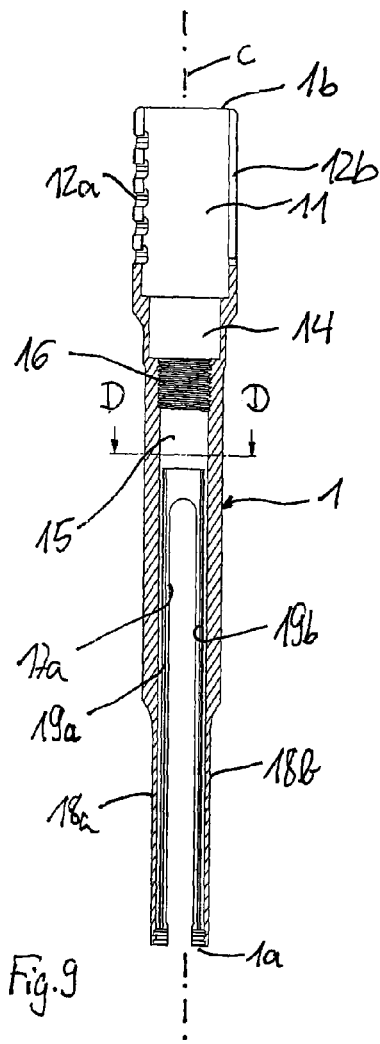
FIG. 9 shows a cross-sectional view of the first sleeve of FIG. 6, the cross-section taken along line B-B in FIG. 8.

The first sleeve 1 includes two elongate substantially U-shaped slits 17a, 17b, as shown, for example, in FIG. 9. The U-shaped slits 17a, 17b have a reverse or inverted U-shape compared to the recess 204 in the receiving part 200 when the receiving part 200 is attached to the extension device. The U-shaped slits 17a, 17b are offset from each other by 180° and extend from the front end 1a toward the rear end 1b up to a distance from the second section 14 of the first sleeve 1. The longitudinal slits 17a, 17b have a width in a circumferential direction around the longitudinal axis c that is greater than a diameter of the rod (not shown) and have the function of permitting the rod to be inserted therethrough. The width of the slits 17a, 17b may be substantially the same as the width of the U-shaped recess 204 in the receiving part 200. By means of the slits 17a, 17b, the first sleeve 1 includes two free legs 18a, 18b that are configured to cooperate with the free legs 205a, 205b of the receiving part 200. At each of the legs 18a, 18b, the inner surface of the third section 15 of the first sleeve 1 includes a longitudinally extending substantially cylinder segment-shaped guiding recess 19a, 19b, into which a portion of the second sleeve 2 can extend to be guided therein. The guiding recesses 19a, 19b extend in a longitudinal direction beyond the longitudinal recesses 17a, 17b toward the rear end 1b of the first sleeve, as can be seen in FIG. 9.

Figure 7:
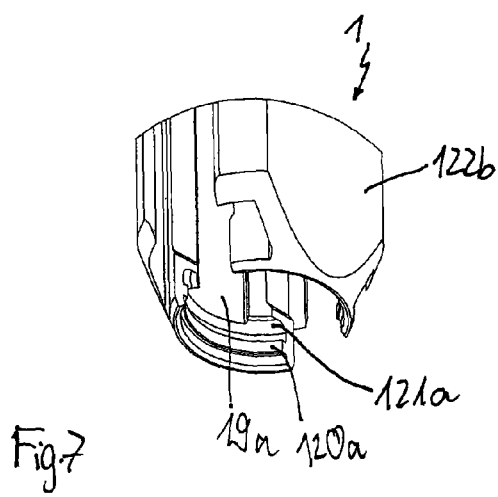
FIG. 7 shows a perspective view from below a front end portion of the first sleeve of FIG. 6.
Figure 10:
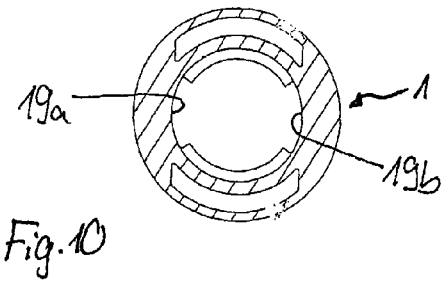
FIG. 10 shows a cross-sectional view of the first sleeve of FIG. 6, the cross-section taken along line D-D in FIG. 9.

At a distance from the front end 1a, each of the legs 18a, 18b has a projection 120a, 120b that extends in a circumferential direction around the longitudinal axis c from one slit 17a to the opposite slit 17b, as best seen in FIG. 7. The shape of the circumferential projections 120a, 120b are substantially complementary to the shape of the circumferential grooves 206a, 206b of the receiving part 200, as can be seen in particular in FIG. 19b. Upper surfaces of the projections 120a, 120b that face toward the rear end 1b may be inclined or reduced in diameter or width toward the rear end 1b to match the complementary inclined upper walls 206a', 206b' of the grooves 206a, 206b. Lower surfaces of the circumferential projections 120a, 120b may be perpendicular to the longitudinal axis c or also similarly inclined toward the rear end 1b. Between each of the projections 120a, 120b and the end of the guiding recesses 19a, 19b, there is an inner surface portion 121a, 121b that substantially matches an outer surface portion of the receiving part 200 between the grooves 206a, 206b and the top end 200a.

By means of the legs 18a, 18b, the first sleeve 1 is slightly flexible in a radial direction, so that the first sleeve 1 can be snapped onto the legs 205a, 205b of the receiving part 200.

An outer diameter of the first sleeve 1 may vary between the rear end 1b and the front end 1a. The first sleeve 1 may have a greatest outer diameter in the first section 11 followed by one or more successively decreasing outer diameters toward the front end 1a, as shown in FIG. 9. In addition, flattened outer surface portions 122a, 122b may be provided at an outer surface of the legs 18a, 18b that extend from the front end 1a toward the rear end 1b for cooperation with a tool (not shown).

The total length of the first sleeve 1 is such that when the bone anchor is inserted into the bone and the first sleeve 1 is attached to the receiving part 200, the rear end 1b and first section 11 are sufficiently above the operation site when the extension device is used.

Referring now to FIGS. 11a to 12, the second sleeve 2 includes a front end or distal end 2a and an opposite rear end or proximal end 2b. The second sleeve 2 may have a substantially constant outer diameter. Adjacent to the rear end 2b, the second sleeve 2 includes a first portion 21 with a circumferentially closed cylindrical surface, where the first portion 21 is configured to engage the interlocking bushing 3. A plurality of coaxially extending slits 22 that are open to the rear end 2b and that extend to a distance from the rear end 2b are provided in the second sleeve 2. The plurality of coaxially extending slits 22 render the first portion 21 flexible in such a way that the first portion 21 can elastically snap onto a portion of the interlocking bushing 3 and hold the interlocking bushing 3 by friction. At a first distance from the rear end 2b, a circumferentially extending annular projection 23 is provided that projects radially inward. The annular projection 23 cooperates with a corresponding depression or recess at the interlocking bushing 3 to inhibit an inadvertent removal of the interlocking bushing 3 from the second sleeve 2. At a second distance from the rear end 2b, a stop 21a, for example in the form of an annular shoulder, is provided that limits how far the interlocking bushing 3 can be inserted into the second sleeve 2 and provides an abutment for the interlocking bushing 3 when the interlocking bushing is screwed into the first sleeve 1. An outer diameter of the first portion 21 of the second sleeve 2 is such that the first portion 21 fits into the third section 15 of the first sleeve 1.

Two recesses 24a, 24b with substantially rectangular cross-sections extend from the front end 2a through the second sleeve 2 up to the first portion 21. The recesses have a size such that two opposite legs 25a, 25b are formed that fit into the guiding recesses 19a, 19b of the first sleeve 1. The legs 25a, 25b have a length such that the legs 25a, 25b can extend beyond the upper closed ends of the U-shaped slits 17a, 17b of the first sleeve 1 in a direction toward the rear end 1b of the first sleeve 1, for example, when the second sleeve 2 is inserted into the first sleeve 1.

The front end 2a of the second sleeve 2 includes substantially flat surface portions 26a, 26b on each of the legs 25a, 25b that are configured to cooperate with substantially flat surface portions on the top end 200a of the receiving part 200. The front end 2a includes projections 27a, 27b on each of the legs 25a, 25b, respectively, that are configured to cooperate with the recesses 207a, 207b at the free ends of the legs 205a, 205b of the receiving part 200. The projections 27a, 27b have a complementary shape to the shape of the recesses 207a, 207b of the receiving part 200. As can be seen in FIG. 11b, side surfaces of the projections 27a, 27b that face toward the longitudinal axis of the second sleeve 2 are flush with the inner surfaces of other portions of the legs 25a, 25b. In addition, outer surfaces of the projections 27a, 27b are slightly recessed with respect to outer surfaces of other portions of the legs 25a, 25b. The shapes of the projections 27a, 27b are substantially arc-shaped with rounded edges like the corresponding recesses 207a, 207b in the receiving part 200. In a circumferential direction around the longitudinal axis of the second sleeve 2, the projections 27a, 27b are each arranged substantially in the middle of each respective leg 25a, 25b.

Figure 13:
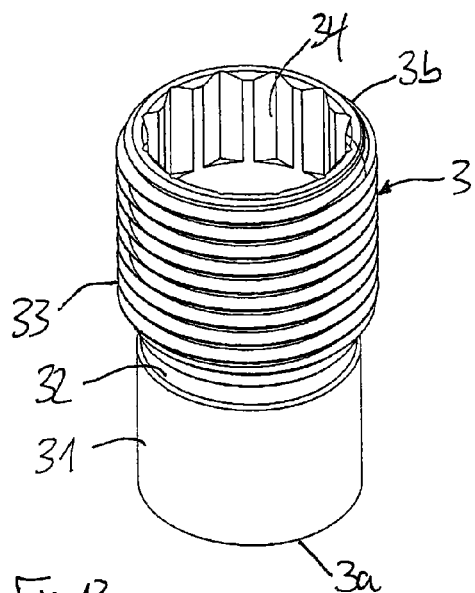
FIG. 13 shows a perspective view of an interlocking bushing of the extension device of FIGS. 1 and 2.
Figure 14:
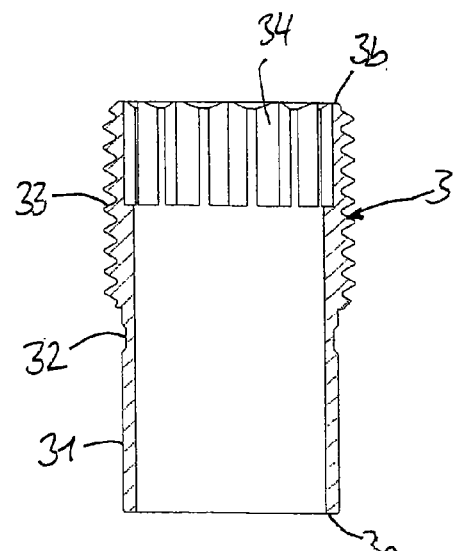
FIG. 14 shows a cross-sectional view of the interlocking bushing of FIG. 13, the cross-section taken in a plane containing a cylinder axis of the bushing.

Turning now to FIGS. 13 and 14, the interlocking bushing 3 includes a front end or distal end 3a, a rear end or proximal end 3b, and a cylindrical section 31. The cylindrical section 31 is adjacent to the front end 3a and has an outer diameter that is substantially the same as the inner diameter of the first portion 21 of the second sleeve 2. The inner diameter of the first portion 21 of the second sleeve 2 and the cylindrical section 31 of the bushing 3 may be sized such that the bushing 3 is held in the second sleeve 2 by friction. The cylindrical section 31 has a smooth outer surface. Adjacent to the cylindrical section 31, there is a groove 32 for engaging with the annular projection 23 of the second sleeve 2. Adjacent to the rear end 3b, a threaded portion 33 with an external thread is provided that is configured to cooperate with the threaded section 16 of the first sleeve 1. An inner diameter of the bushing 3 may be substantially constant and sized such that a locking member for fixing the rod in the receiving part 200 can be inserted therethrough. Adjacent to the rear end 3b, the inner surface of the bushing 3 includes an engagement portion 34, for example, a plurality of longitudinally extending grooves and projections for engagement with a tool.

Figure 15:
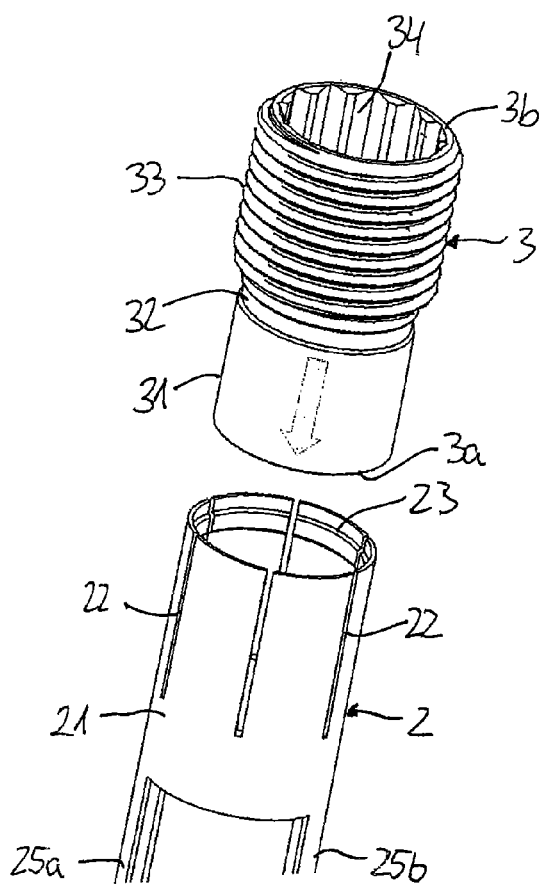
Figure 16:
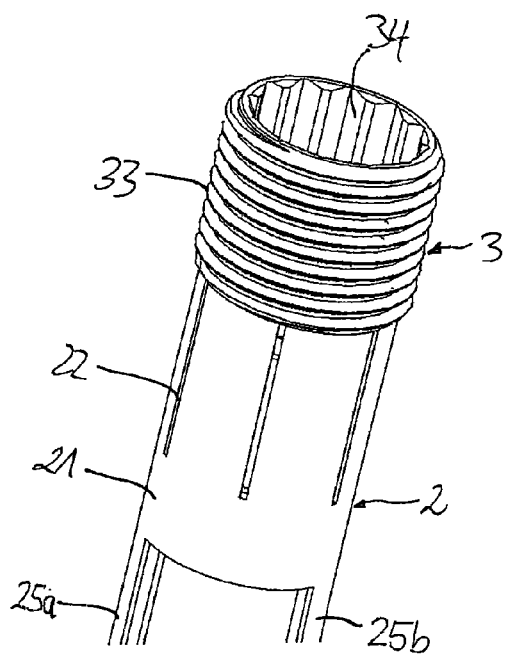
FIG. 16 shows a perspective view of the interlocking bushing and the first sleeve of FIG. 15 mounted together.

The assembly of the second sleeve 2 and the interlocking bushing 3 is shown in FIGS. 15 and 16. The cylindrical portion 31 of the interlocking bushing 3 is pushed into the first portion 21 of the second sleeve 2 until the inwardly projecting annular projection 23 on the second sleeve 2 snaps into the groove 32 of the interlocking bushing 3. As a result, the interlocking bushing 3 is coupled to the second sleeve 2 in such a manner that rotational motion of the interlocking bushing 3 relative to the second sleeve 2 is possible. In addition, axial movement of the interlocking bushing 3 relative to the second sleeve 2 is inhibited due, for example, to the interlocking bushing 3 abutting against the stop 21a provided in the second sleeve 2.

The assembly including of the second sleeve 2 and the interlocking bushing 3, as shown in FIG. 16, is then inserted into the first sleeve 1 from the rear end 1b until the threaded portion 33 of the interlocking bushing 3 engages the threaded section 16 of the first sleeve 1. The legs 25a, 25b are guided in the guiding recesses 19a, 19b in the first sleeve 1. By means of this, the extension device is assembled. When the interlocking bushing 3 is secured into the threaded section 16 of the first sleeve 1, the connection between the second sleeve 2 and the first sleeve 1 via the interlocking bushing is a rigid connection.

Referring now to FIGS. 17 to 23, the attachment of the extension device to a polyaxial bone anchor will be described. As shown in FIG. 17, the front end 1a of the first sleeve 1 of the extension device is moved toward the receiving part 200. Then, as depicted in FIG. 18, the legs 18a, 18b of the first sleeve 1 are spread to a certain extent when they touch the top end 200a of the receiving part 200, and by further downward movement of the extension device, the circumferential projections 120a, 120b of the legs 18a, 18b of the first sleeve 1 snap into the circumferential grooves 206a, 206b of the receiving part 200. When the projections 120a, 120b engage the grooves 206a, 206b, axial movement of the first sleeve 1 in a direction away from the receiving part 200 is inhibited.

Then, as shown in FIGS. 19a and 19b, the second sleeve 2 is moved relative to the first sleeve 1 toward the receiving part 200 by screwing the interlocking bushing 3 further toward the front end 1a of the first sleeve 1. When the projections 27a, 27b of the second sleeve 2 enter the corresponding recesses 207a, 207b at the top end 200a of the receiving part 200, rotational movement of the second sleeve 2 and the first sleeve 1 relative to the receiving part 200 is inhibited. Referring to FIGS. 20 to 23, a step of moving the second sleeve 2 relative to the first sleeve 1 is shown. In FIG. 20, the position of the second sleeve 2 relative to the first sleeve 1, which is already attached to the receiving part 200, is such that the projections 27a, 27b of the second sleeve 2 are above the recesses 207a, 207b of the receiving part 200. At this time, the interlocking bushing 3 extends slightly into the second section 14 of the first sleeve 1, as seen in FIG. 21. Then, as seen in FIG. 22, the projections 27a, 27b fully enter the recesses 207a, 207b. This is achieved, as shown in FIG. 23, by rotating the interlocking bushing 3 so that the interlocking bushing 3 advances distally or downwardly in the threaded section 16 of the first sleeve 1. Because the interlocking bushing 3 abuts against the stop 21a in the second sleeve 2, the interlocking bushing 3 pushes the second sleeve 2 forward when the interlocking bushing 3 moves. The second sleeve 2 can rotate relative to the interlocking bushing 3 so that the alignment between the legs 18a, 18b of the first sleeve 1 and the legs 25a, 25b of the second sleeve 2 is maintained. A further rotation of the interlocking bushing 3 presses the flat surface portions 26a, 26b of the front end 2a of the second sleeve 2 onto the free flat end surfaces of the receiving part 200. Through this and the engagement of the projections 120a, 120b of the first sleeve 1 with the grooves 206a, 206b of the receiving part 200, the first sleeve 1 is interlocked with the receiving part 200 and with the second sleeve 2 to provide a safe and strong connection between the extension device and the receiving part 200. In such a configuration, the insertion of the rod and locking screw can take place, as well as surgical steps thereafter, such as compression and distraction steps utilizing the extension device.

Rotating the interlocking bushing 3 in an opposite direction, moves the interlocking bushing 3 away from the front end 1a of the first sleeve 1, releases the interlocking connection, and permits retraction of the projections 27a, 27b of the second sleeve 2 out of the recesses 207a, 207b. The extension device may be detached from the receiving part 200. In some embodiments, the second sleeve 2 together with the interlocking bushing 3 can first be removed from the first sleeve 1, and then a tool for detaching the first sleeve 1 from the receiving part 200 can then be used to disengage the circumferential projections 120a, 120b from the grooves 206a, 206b of the receiving part 200.

A second embodiment of a system including a polyaxial bone anchor and an extension device is shown in FIGS. 24 to 27. Parts and portions of the second embodiment that are identical or similar to that of the first embodiment are marked with identical reference numerals, and the descriptions thereof will not be repeated. The second embodiment of the extension device differs from the first embodiment in the design of the front portions of the first sleeve and the second sleeve. The receiving part of the second embodiment also differs from the receiving part of the first embodiment.

The extension device according to the second embodiment includes a first sleeve 1', a second sleeve 2', and an interlocking bushing 3 that is the same as the interlocking bushing 3 in the first embodiment. As can be seen in FIG. 24, a receiving part 200' includes, in addition to the circumferential grooves 206a, 206b on each of the legs 205a, 205b, coaxially extending recesses 210a, 210b that are open toward the top end 200a and that extend in a direction parallel to the central axis C. The recesses 210a, 210b are provided in the outer surfaces of the legs 205a, 205b and do not completely extend through the walls of the legs 205a, 205b. The respective position of each of the recesses 210a, 210b is substantially in the center of each leg 205a, 205b. Furthermore, the recesses 210a, 210b extend through and beneath the circumferential grooves 206a, 206b in the direction of the bottom end 200b. The contour of each of the recesses 210a, 210b is substantially rectangular, but any other shape that achieves the result of providing an abutment against rotational motion of the first sleeve 1' may be contemplated.

Referring to FIGS. 25 and 26, the first sleeve 1' includes two projections 129a, 129b that extend from the front end 1a in a direction parallel to the longitudinal axis c and that are positioned, sized and shaped to be complementary to the recesses 210a, 210b of the receiving part 200'. As depicted in FIG. 26, the projections 129a, 129b project slightly over or past the arc-shaped end surface of each leg 18a, 18b of the first sleeve 1' in the longitudinal direction c. The engagement of the projections 129a, 129b with the corresponding coaxial recesses 210a, 210b of the receiving part 200' generates a form fit connection that is configured to inhibit rotational movement of the first sleeve 1' relative to the receiving part 200'.

The second sleeve 2' differs from the second sleeve 2 of the first embodiment in that the projections 27a, 27b are omitted. As such, the front end 2a of the second sleeve 2' includes two arc-shaped flat surfaces 26a', 26b' respectively corresponding to each of the legs 25a, 25b, as shown in FIG. 27.

The attachment of the second embodiment of the extension device to the receiving part 200' will be explained with reference to FIGS. 28 to 30b. First, as shown in FIG. 28, front end 1a of the first sleeve 1' of the extension device according to the second embodiment is moved toward the receiving part 200' such that the legs 18a, 18b of the first sleeve 1' are aligned with the legs 205a, 205b of the receiving part 200'. A further downward movement of the first sleeve 1' causes an engagement of the coaxial projections 129a, 129b of the first sleeve 1' with the coaxial recesses 210a, 210b of the receiving part 200', as well as a snap in of the circumferential projections 120a, 120b into the circumferential grooves 206a, 206b of the receiving part 200'. Once the grooves 206a, 206b and the recesses 210a, 210b are in full engagement with the first sleeve 1', axial and rotational movement of the first sleeve 1' relative to the receiving part 200' are inhibited. Thereafter, the second sleeve 2' is advanced toward the receiving part 200' by rotating the interlocking bushing 3 until the free end surfaces 26a', 26b' abut against the free end surface of the first end 200a of the receiving part 200' as shown in detail in FIG. 30b. Final tightening of the interlocking bushing 3 generates a force-fit connection between the abutting surfaces of the second sleeve 2' and the receiving part 200' and an interlocking of the extension device relative to the receiving part 200'. Rotating the interlocking bushing 3 in the opposite direction causes the connection to be released.

Figure 31:
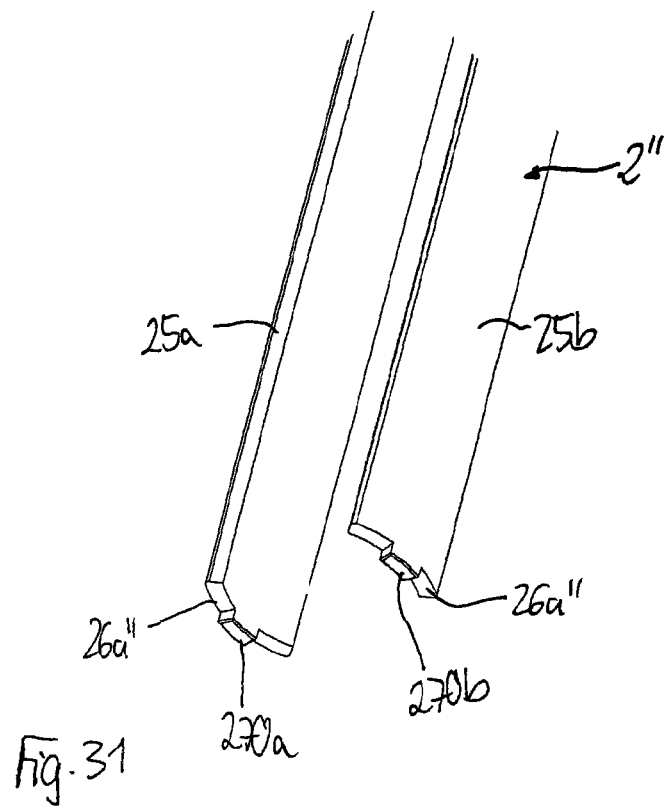
FIG. 31 shows a perspective view of a front end portion of a modified embodiment of a second sleeve of an extension device.

A modified embodiment of the design of the second sleeve is shown in FIG. 31. The second sleeve 2" may have at the front end 2a, instead of the projections 27a, 27b according to the first embodiment, projections 270a, 270b that are flush with the inner and outer surfaces of the legs 25a, 25b. The projections 270a, 270b have an arc-shape with a flat front surface, and either perpendicular side walls or inclined side walls. The projections 270a, 270b may be more easily manufactured by cutting away a portion of the legs 25a, 25b. A corresponding receiving part has complementary shaped recesses for engagement with the projections 270a, 270b.

Figure 32:
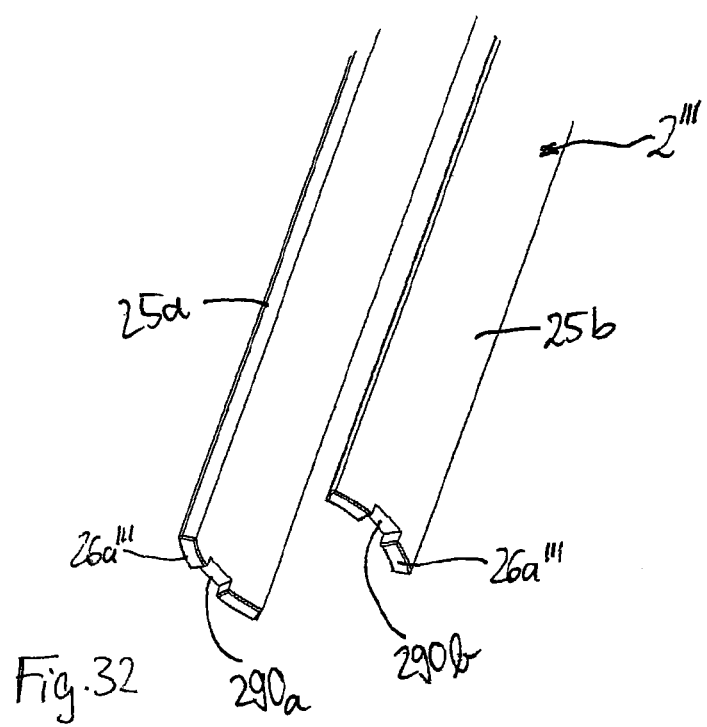
FIG. 32 shows a perspective view of a front end portion of another modified embodiment of a second sleeve of an extension device.

A still further modified embodiment of the second sleeve is shown in FIG. 32. The second sleeve 2'" includes, at the front end 2a, two recesses 290a, 290b on the legs 25a, 25b. A corresponding receiving part (not shown) can have a complementary shape to achieve a form-fit connection.

A third embodiment of the extension device and of a system including the extension device and a polyaxial bone anchor is shown in FIGS. 34 to 38. A receiving part 200" that is adapted to cooperate with the extension device of the third embodiment is similar to the receiving part 200 of the first embodiment. Parts that are identical or similar to the corresponding parts of the first embodiment are indicated with the same reference numerals, and the descriptions thereof will not be repeated. The receiving part 200" includes a pair of longitudinal grooves 212a at one side of the U-shaped recess 204 and a pair of longitudinal grooves 212b at the opposite side of the U-shaped recess 204. Each respective pair of grooves 212a, 212b are spaced apart from each other in the circumferential direction. Furthermore, the grooves 212a, 212b extend from the top end 200a at the outer wall of the receiving part 200" on either side of the recesses 207a, 207b. The grooves 212a, 212b are open toward the top end 200a and have a decreasing depth toward their opposite closed ends that are located at a distance from the top end 200a. The cross-sections of the longitudinal grooves 212a, 212b are substantially rectangular. As can be seen in particular in FIGS. 34 and 36, the longitudinal grooves 212a, 212b intersect the circumferentially extending grooves 206a, 206b. The purpose of the longitudinal grooves 212a, 212b is to cooperate with respective corresponding longitudinally extending pairs of ribs 112a, 112b of a first sleeve 1" of the extension device, in order to provide a form-fit connection.

The extension device according to the third embodiment includes a first sleeve 1" that is similar to the first sleeve 1 of the first embodiment. In the following description, only the differences between the third embodiment and the first embodiment will be explained. The first sleeve 1" includes a pair of ribs 112a and a pair of ribs 112b respectively located on the legs 18a, 18b at positions that correspond in a circumferential direction to the positions of the longitudinal grooves 212a, 212b of the receiving part 200". The ribs 112a, 112b protrude inwardly from the legs 18a, 18b, downwardly or distally from the front end 1a, and have a shape that substantially matches the shape of the grooves 212a, 212b of the receiving part 200". As can be seen in particular in FIG. 38, outer surfaces of the ribs 112a, 112b taper and reduce in width toward a free ends of the ribs 112a, 112b, such that, the vertical cross-section of each of the ribs 112a, 112b is substantially triangular when viewed from a circumferential direction.

From each of the longitudinal ribs 112a, 112b, transverse thickened rib portions 123a, 123b extend outwardly in a circumferential direction. The transverse rib portions 123a, 123b are located at a distance from the front end 1a of the first sleeve 1" that corresponds to the distance of the circumferentially extending grooves 206a, 206b from the top end 200a of the receiving part 200". The transverse rib portions 123a, 123b are located at the same distance from the front end 1a of the first sleeve 1" as the circumferential projections 120a, 120b.

The second sleeve 2 of the third embodiment may be identical to the second sleeve 2 of the first embodiment that has the projections 27a, 27b for engaging the recesses 207a, 207b on the top end 200a of the receiving part 200".

By means of the longitudinal ribs 112a, 112b that engage the longitudinal grooves 212a, 212b, respectively, the strength of the connection between the extension device and the receiving part 200" is enhanced. The longitudinal ribs and grooves allow the application of a high torque to the receiving part by the extension device.

In use, the first sleeve 1" is snapped over the receiving part 200" until the form-fit connection between the circumferential projections 120a, 120b with the transverse portions 123a, 123b and the circumferential grooves 206a, 206b is established. In addition, the longitudinal ribs 112a, 112b engage the longitudinal grooves 212a, 212b. Thereby, rotation between the extension device and the receiving part 200" is prevented.

It shall be noted that for the second sleeve 2 of the third embodiment, the second sleeve 2', 2", 2'" described with respect to the other embodiments may instead be used. The number of cooperating longitudinal ribs and grooves may also vary. In one or more embodiments, at least one rib and one groove are provided on each leg 25a, 25b, but more than two ribs and grooves may also be provided.

The parts of the extension device are made of a body-compatible material, such as titanium or stainless steel, a body-compatible metal alloy, for example a Ti—Ni alloy, such as Nitinol, or a body-compatible plastic material, such as PEEK.

Figure 33:
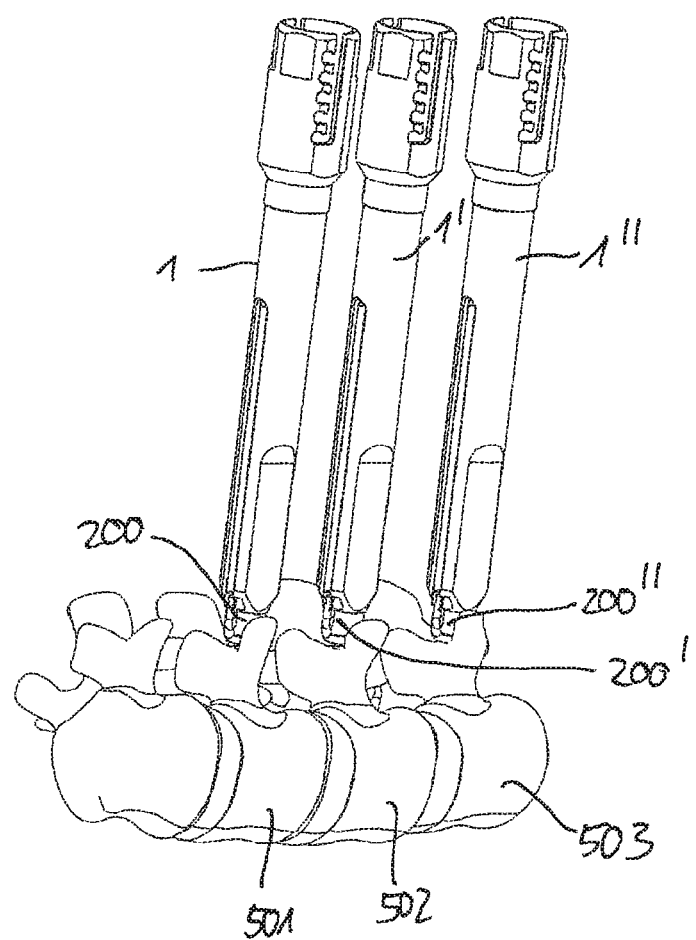
FIG. 33 shows a perspective view of a section of the spinal column with inserted pedicle screws and attached extension devices according to an embodiment of the invention.
Figure 37:
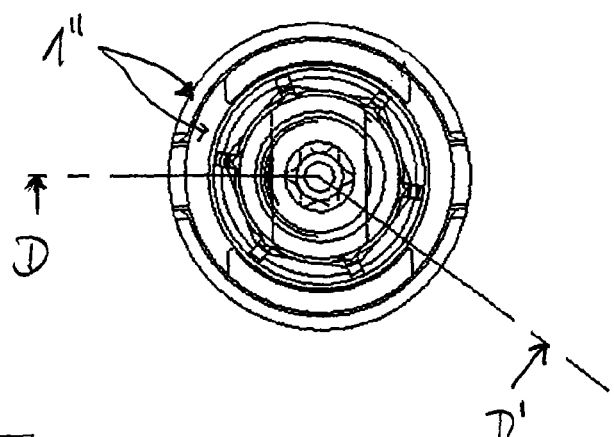
FIG. 37 shows a top view of the extension device and bone anchor according to the third embodiment.
Figure 38:
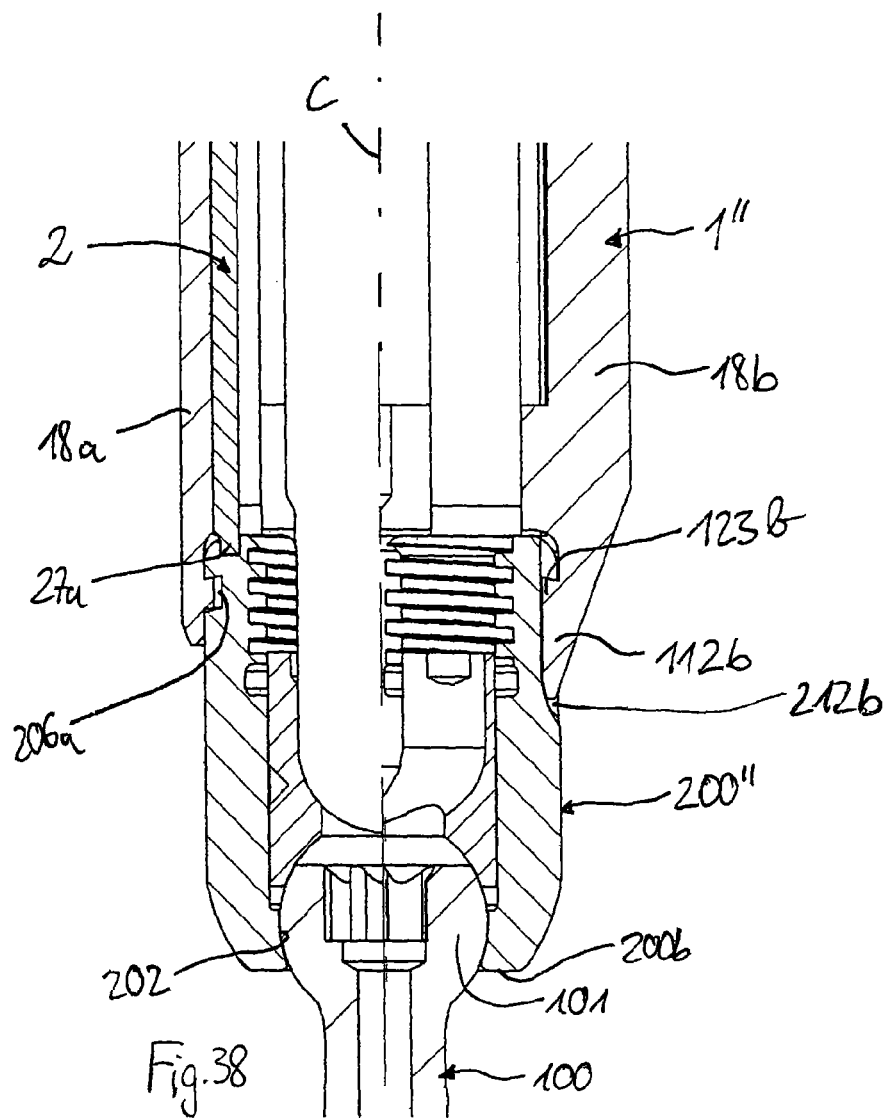
FIG. 38 shows an enlarged cross-sectional view of the front end portion of the extension device according to the third embodiment and the bone anchor with the receiving part according to the third embodiment, the cross-section taken along line D-D' in FIG. 37.

In clinical use, as shown in FIG. 33, an extension device according to one or more of the embodiments described above is attached to a corresponding receiving part 200, 200', 200" of respective polyaxial bone anchors that have been inserted into pedicles of a vertebra 501, 502, 503. The legs of the sleeves of the extension device are aligned with the legs of the receiving part, such that by rotating the extension devices, the channels of the receiving parts of the bone anchors can be aligned to permit easier insertion of a rod. Because the connection between the receiving part and the extension device is robust and safe, an easy alignment using the extension devices is possible. Thereafter, the rod is inserted (not shown) and fixed with a locking screw that is guided through the first and second sleeves of each extension device until the locking screw can be screwed between the legs 205a, 205b of the receiving parts. By applying an instrument to the extension device, a compression or distraction procedure can also be performed using minimally invasive techniques.

Other modifications of the above described embodiments may also be contemplated. It shall be noted, that the shapes of the complementary engaging structures of the first sleeve and the receiving part, as well as of the second sleeve and the receiving part, can be modified and are not limited to the exact shapes shown in the embodiments.

The extension device can also be used with any bone anchor that includes a receiving part, such as polyaxial bone anchors or a monoaxial bone anchors, and to different shapes of receiving parts. Anchors with inner compression members or outer rings may be used with the extension device, so long as an engagement structure is provided at an upper end of the receiving part that cooperates with a corresponding structure of the extension device.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. An extension device for a bone anchor, wherein the bone anchor comprises an anchoring section for anchoring to a bone and a receiving part connected to the anchoring section, the receiving part comprising a central axis and a channel for receiving a rod, the extension device comprising:
   a first sleeve having a first sleeve axis, wherein the first sleeve is configured to be detachably coupled to the receiving part;
   a second sleeve configured to contact the receiving part when the second sleeve is positioned in the first sleeve; and
   a coupling member configured to connect the first sleeve to the second sleeve, wherein when the coupling member is connected to the first sleeve, the entire coupling member is in the first sleeve;
   wherein the first sleeve is configured to contact the receiving part to restrict translational movement of the first sleeve relative to the receiving part along the central axis,
   wherein the second sleeve is configured to contact the receiving part to restrict rotational movement of the second sleeve relative to the receiving part, and
   wherein the coupling member is configured to axially advance in the first sleeve together with the second sleeve along the first sleeve axis.

2. The extension device of claim 1,
   wherein the first sleeve comprises a first end, an opposite second end, and an attachment structure adjacent the first end configured to detachably couple to the receiving part,
   wherein the coupling member comprises an advancement structure configured to couple the coupling member to the first sleeve, and
   wherein when the advancement structure of the coupling member is coupled to the first sleeve, the coupling member and the second sleeve are configured to advance along the first sleeve axis to a given position closer to the first end of the first sleeve.

3. The extension device of claim 2, wherein the coupling member is a bushing and the advancement structure comprises threads.

4. The extension device of claim 3, wherein the second sleeve is configured to be coupled to the first sleeve in a rigid manner.

5. The extension device of claim 1, wherein the coupling member is coupled to the second sleeve such that the coupling member can rotate with respect to the second sleeve.

6. The extension device of claim 1, wherein the second sleeve comprises an abutment configured to restrict the coupling member from moving axially relative to the second sleeve.

7. A spinal stabilization system for use with minimally invasive surgery comprising a system with at least two bone anchors and an extension device for each bone anchor according to claim 1.

8. The extension device of claim 1, wherein at least a portion of the coupling member is configured to be positioned in the second sleeve.

9. The extension device of claim 1, wherein a rear end of the first sleeve comprises at least one longitudinal slit and a plurality of notches extending from the longitudinal slit for latching with a tool to fix an inserted rod.

10. An extension device system comprising an extension device and a bone anchor,
the bone anchor comprising:
an anchoring section for anchoring to a bone and a receiving part connected to the anchoring section, the receiving part comprising a central axis and a channel for receiving a rod, wherein sidewalls of the channel form two free legs,
the extension device comprising:
a first sleeve having a first sleeve axis, wherein the first sleeve is configured to be detachably coupled to the receiving part;
a second sleeve having a second sleeve axis, wherein the second sleeve is configured to be positioned in the first sleeve with the second sleeve axis coaxial with the first sleeve axis; and
a coupling member configured to couple to the second sleeve and configured to connect the first sleeve to the second sleeve, wherein when the coupling member is coupled to the second sleeve, the coupling member is restricted from moving axially relative to the second sleeve along the second sleeve axis;
wherein the first sleeve is configured to couple to the receiving part and prevent translational movement of the first sleeve relative to the receiving part along the central axis,
wherein the second sleeve remains movable along the central axis relative to the first sleeve when the first sleeve is coupled to the receiving part and prevented from translational movement relative to the receiving part,
wherein the second sleeve is configured to be coupled to the receiving part to restrict rotational movement of the second sleeve relative to the receiving part; and
wherein when the coupling member is connected to the first sleeve, the entire coupling member is in the first sleeve.

11. The extension device of claim 10, wherein the first sleeve comprises a protrusion and/or a recess at an inner surface thereof that is configured to engage a complementary structure at an outer surface of the receiving part to provide a form-fit connection between the first sleeve and the receiving part.

12. The extension device of claim 11, wherein the protrusion and/or recess at the first sleeve and the complementary structure at the receiving part are shaped to restrict axial movement of the first sleeve relative to the receiving part along the central axis of the receiving part.

13. The extension device of claim 11, wherein the protrusion and/or recess of the first sleeve is configured to engage the complementary structure of the receiving part to restrict rotational movement of the first sleeve relative to the receiving part about the central axis.

14. The extension device of claim 10, wherein the second sleeve comprises a protrusion and/or a recess at a surface thereof that is configured to engage a complementary structure at a surface of the receiving part to provide a form-fit connection between the second sleeve and the receiving part.

15. The extension device of claim 10, wherein the second sleeve comprises a substantially flat surface portion that is configured to engage a substantially flat surface portion of the receiving part such that friction between the surface portions is generated when the receiving part is rotated relative to the second sleeve.

16. The extension device of claim 10, wherein the first sleeve comprises a first end and an opposite second end and wherein the first sleeve comprises a longitudinal recess that extends in an axial direction and that is open to the second end, wherein a width of the recess of the first sleeve is at least as wide as a width of the channel of the receiving part for receiving the rod.

17. The extension device of claim 10, wherein the second sleeve comprises a first end and an opposite second end and wherein the second sleeve comprises a longitudinal recess that extends in an axial direction and that is open to the second end, wherein a width of the recess of the second sleeve is at least as wide as a width of the channel of the receiving part for receiving the rod.

18. The extension device of claim 10, wherein the first sleeve comprises at least one longitudinally extending rib configured to engage a corresponding longitudinally extending groove in the receiving part to restrict rotational movement of the receiving part relative to the first sleeve about the central axis.

19. The extension device of claim 10, wherein the first sleeve comprises a circumferentially extending rib configured to engage a circumferentially extending groove of the receiving part to restrict axial movement of the first sleeve relative to the receiving part along the central axis.

20. A method of connecting an extension device to a bone anchor, the bone anchor comprising an anchoring section for anchoring to a bone and a receiving part connected to the anchoring section, the receiving part comprising a central axis and a channel for receiving a rod, the extension device comprising a first sleeve having a first sleeve axis, a second sleeve having a second sleeve axis, and a coupling member configured to connect the first sleeve to the second sleeve, the method comprising:
connecting the coupling member to the second sleeve, wherein the coupling member is rotationally movable relative to the second sleeve axis and is restricted from moving axially relative to the second sleeve;
positioning the second sleeve in the first sleeve;
attaching the first sleeve to the receiving part such that the first sleeve axis is coaxial with the central axis of the receiving part and translational movement of the first sleeve relative to the receiving part along the central axis is restricted;

advancing the second sleeve relative to the first sleeve via the coupling member such that the entire coupling member is in the first sleeve; and contacting the receiving part with the second sleeve to restrict rotational movement of the second sleeve relative to the receiving part.

21. An extension device for a bone anchor, wherein the bone anchor comprises an anchoring section for anchoring to a bone and a receiving part connected to the anchoring section, the receiving part comprising a central axis and a channel for receiving a rod, the extension device comprising:

a first sleeve comprising a first end, an opposite second end, a first sleeve axis extending between the first end and the second end, and an engagement structure adjacent the first end, the engagement structure comprising a curved inner profile and an axial projection each configured to detachably couple to the receiving part, the curved inner profile curving in a circumferential direction around the first sleeve axis and having a length in the circumferential direction that is greater than an axial length of the curved inner profile;

a second sleeve configured to be positioned in the first sleeve; and a coupling member separate from the first sleeve and the second sleeve and configured to connect the first sleeve to the second sleeve;

wherein the first sleeve is configured to be coupled to the receiving part to restrict translational and rotational movement of the first sleeve relative to the receiving part along the central axis via the curved inner profile and the axial projection of the first sleeve; and wherein the second sleeve is configured to be coupled to the receiving part to restrict rotational movement of the second sleeve relative to the receiving part.

22. The extension device of claim 21, wherein the engagement structure of the first sleeve comprises a circumferentially extending rib.

* * * * *